US00PP36562P2

(12) United States Plant Patent
Spil

(10) Patent No.: US PP36,562 P2
(45) Date of Patent: Mar. 18, 2025

(54) ***ECHINACEA* PLANT NAMED 'IFECSSMS'**

(50) Latin Name: *Echinacea hybrida*
Varietal Denomination: IFECSSMS

(71) Applicant: INNOFLORA PLANT BREEDING B.V., Heerhugowaard (NL)

(72) Inventor: Glenn Spil, Zuidermeer (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 18/613,007

(22) Filed: Mar. 21, 2024

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 6/1448; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Echinacea* plant named 'IFECSSMS', characterized by its relatively compact and upright plant habit; moderately vigorous to vigorous growth habit; freely branching habit; strong flowering stems; numerous single type inflorescences with bright yellow-colored ray florets with red-colored receptacle spines; and good garden performance.

2 Drawing Sheets

Figure 1:
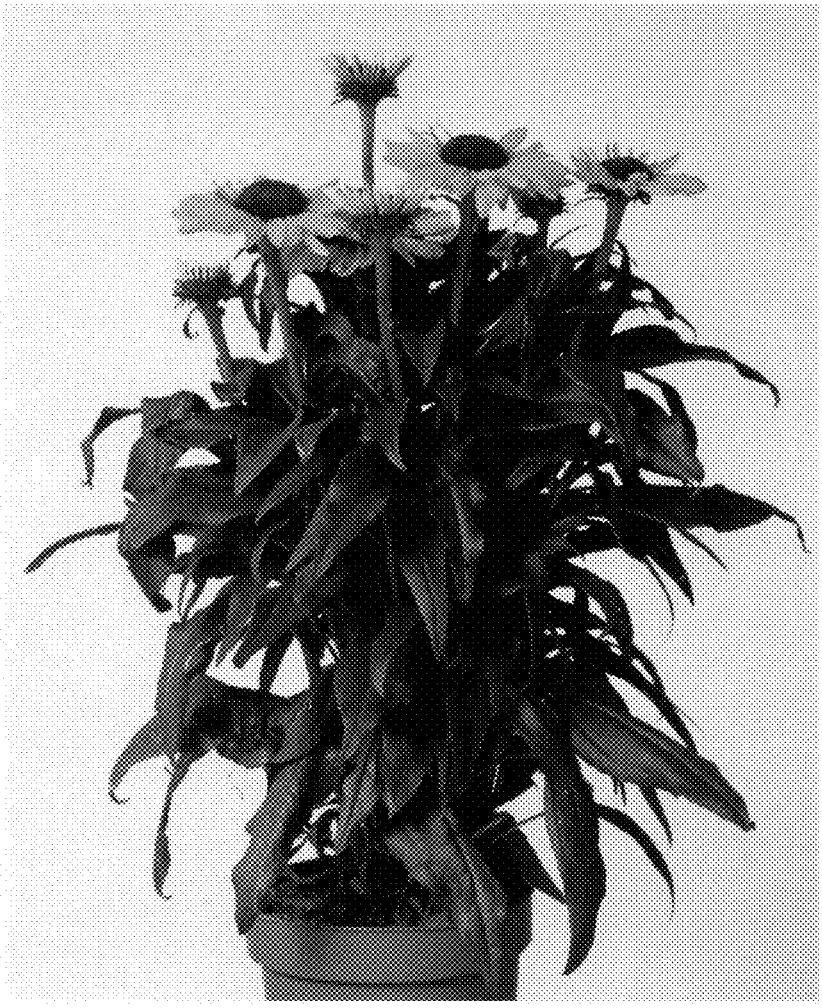

Botanical designation: *Echinacea hybrida.*
Cultivar denomination: 'IFECSSMS'.

STATEMENT REGARDING PRIOR DISCLOSURES BY INVENTOR & APPLICANT/ASSIGNEE

A Polish Plant Breeder's Rights application for the instant plant was filed by the Applicant/Assignee, Innoflora Plant Breeding B.V. of Heerhugowaard, The Netherlands on Jan. 17, 2024, application number O 2260. Foreign priority is not claimed to this application.

An European Community Plant Breeder's Rights application for the instant plant was filed by the Applicant/Assignee, Innoflora Plant Breeding B.V. of Heerhugowaard, The Netherlands on Mar. 4, 2024, application number 2024/0584. Foreign priority is not claimed to this application.

The Inventor and Applicant/Assignee assert that no sales, offers for sale or public distribution of the instant plant occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Echinacea* plant, botanically known as *Echinacea hybrida*, and hereinafter referred to by the name 'IFECSSMS'.

The new *Echinacea* plant is a product of a planned breeding program conducted by the Inventor in Heerhugowaard, The Netherlands. The objective of the breeding program is to develop new vigorous and freely flowering *Echinacea* plants with large inflorescences with unique and attractive ray floret coloration.

The new *Echinacea* plant originated from an open-pollination in July, 2018 in Heerhugowaard, The Netherlands of a proprietary selection of *Echinacea hybrida* identified as code number 009-15-K007-05, not patented, as the female, or seed, parent with an unknown proprietary selection of *Echinacea hybrida*, as the male, or pollen, parent. The new *Echinacea* plant was discovered and selected by the Inventor as a single flowering plant from within the progeny of the stated open-pollination grown in a controlled greenhouse environment in Heerhugowaard, The Netherlands in August, 2019.

Asexual reproduction of the new *Echinacea* plant by in vitro meristem culture in a controlled environment in Heerhugowaard, The Netherlands since September, 2019 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'IFECSSMS'. These characteristics in combination distinguish 'IFECSSMS' as a new and distinct *Echinacea* plant:

1. Relatively compact and upright plant habit.
2. Moderately vigorous to vigorous growth habit.
3. Freely branching habit.
4. Strong flowering stems.

5. Numerous single type inflorescences with bright yellow-colored ray florets with red-colored receptacle spines.
6. Good garden performance.

Plants of the new *Echinacea* can be compared to plants of the female parent selection. Plants of the new *Echinacea* differ primarily from plants of the female parent selection in the following characteristics:

1. Plants of the new *Echinacea* are taller than plants of the female parent selection.
2. Inflorescences of plants of the new *Echinacea* have a single whorl of ray florets whereas inflorescences of plants of the female parent selection have two whorls of ray florets.
3. Ray florets of plants of the new *Echinacea* are bright yellow in color whereas ray florets of plants of the female parent selection are purple in color.

Plants of the new *Echinacea* can be compared to plants of *Echinacea hybrida* 'IFECSSTS', disclosed in U.S. Plant Pat. No. 34,433. In side-by-side comparisons, plants of the new *Echinacea* differ primarily from plants of 'IFECSSTS' in the following characteristics:

1. Plants of the new *Echinacea* are taller than plants of 'IFECSSTS'.
2. Inflorescences of plants of the new *Echinacea* have more ray florets than inflorescences of plants of 'IFECSSTS'.

Plants of the new *Echinacea* can also be compared to plants of *Echinacea hybrida* 'Parrot', disclosed in U.S. Plant Pat. No. 31,928. In side-by-side comparisons, plants of the new *Echinacea* differ primarily from plants of 'Parrot' in the following characteristics:

1. Plants of the new *Echinacea* are more freely branching than plants of 'Parrot'.
2. Inflorescences of plants of the new *Echinacea* have more ray florets than inflorescences of plants of 'Parrot'.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet (FIG. 1) is a side perspective view of a typical flowering plant of 'IFECSSMS' grown in a container.

Figure 2:
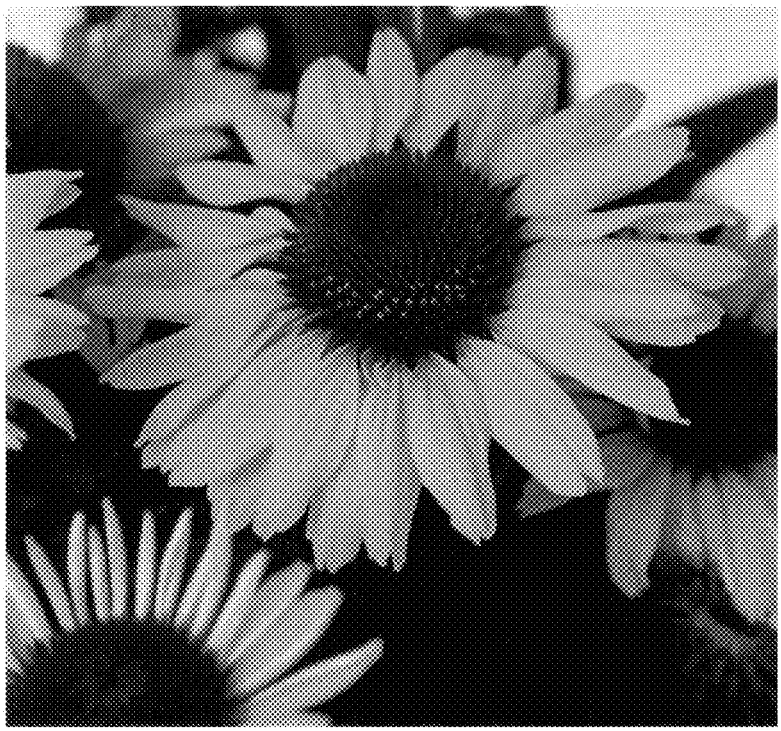

The photograph at the top of the second sheet (FIG. 2) is a close-up view of typical inflorescences of 'IFECSSMS'.

Figure 3:
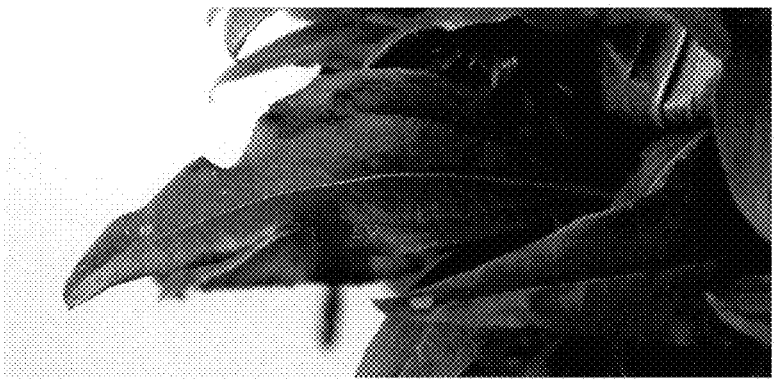

The photograph at the bottom of the second sheet (FIG. 3) is a close-up view of typical leaves of 'IFECSSMS'.

DETAILED BOTANICAL DESCRIPTION

The aforementioned photographs and following observations and measurements describe plants grown during the summer in 19 cm containers in an outdoor nursery in Heerhugowaard, The Netherlands and under cultural practices typically used in commercial *Echinacea* production. During the production of the plants, day temperatures ranged from 18° C. to 32° C. and night temperatures ranged from 8° C. to 20° C. Plants were pinched one time eight weeks after planting and were one year old when the photographs and description were taken. In the following description, color references are made to The Royal Horticultural Society Colour Chart, 2015 Edition, except where general terms of ordinary dictionary significance are used.

Botanical classification: *Echinacea hybrida* 'IFECSSMS'.

Parentage:

*Female parent*.—Proprietary selection of *Echinacea hybrida* identified as code number 009-15-K007-05, not patented.

*Male parent*.—Unknown proprietary selection of *Echinacea hybrida*, not patented.

Propagation:

*Type*.—By in vitro meristem culture.

*Time to initiate roots, summer*.—About twelve days at temperatures about 20° C.

*Time to initiate roots, winter*.—About 16 days at temperatures about 20° C.

*Time to produce a rooted young plant, summer*.—About 36 days at temperatures about 18° C.

*Time to produce a rooted young plant, winter*.—About 42 days at temperatures about 18° C.

*Root description*.—Thick, fleshy; typically white in color, actual color of the roots is dependent on substrate composition, water quality, fertilizer type and formulation, substrate temperature and physiological age of roots.

*Rooting habit*.—Moderately freely branching; sparse.

Plant description:

*Plant form and growth habit*.—Herbaceous perennial; relatively compact and upright plant habit; oblong to obovate in overall shape; freely basal branching habit with about 15 primary lateral branches and about 38 secondary lateral branches developing per plant; moderately vigorous to vigorous growth habit and moderate growth rate.

*Plant height*.—About 54.9 cm.

*Plant diameter or spread*.—About 44.5 cm.

*Lateral branches*.—Length: About 28.6 cm. Diameter: About 1 cm. Internode length: About 2.5 cm. Aspect: Erect to about 10° From vertical. Strength: Strong. Texture: Moderately pubescent; strigose. Color: Close to 144A; slightly blotched, blotches, close to 143A.

Leaf description:

*Basal and cauline leaves*.—Arrangement: Alternate, simple. Length: About 17.2 cm. Width: About 5.1 cm. Shape: Narrowly ovate to lanceolate. Apex: Narrowly acute. Base: Narrowly cuneate. Margin: Irregular shallowly and coarsely dentate-serrate to entire; slightly to moderately undulate. Texture and luster, upper and lower surfaces: Moderately pubescent, strigose and rough; slightly glossy. Venation pattern: Pinnate. Color: Developing leaves, upper surface: Close to 137B. Developing leaves, lower surface: Close to a blend of 146A and 147B. Fully expanded leaves, upper surface: Close to NN137A; venation, close to 146B. Fully expanded leaves, lower surface: Close to 147B; venation, close to 146D.

*Petioles, basal and cauline leaves*.—Length: About 2.4 cm. Diameter: About 3.5 mm by 5.5 mm. Texture, upper surface: Smooth, glabrous; margins, sparsely pubescent; strigose. Texture, lower surface: Sparsely pubescent; strigose. Color, upper surface: Darker than 143A; midvein, close to 146C. Color, lower surface: Close to 137B; midvein, close to 146D.

Inflorescence description:

*Appearance*.—Single type inflorescences with ray and disc florets arranged on a capitulum; inflorescences positioned upright above the foliar plane on mostly upright and strong peduncles.

*Flowering habit*.—Freely flowering habit with about 53 developing and fully developed inflorescences developing per plant.

*Fragrance*.—Faintly fragrant; sweet and pleasant.

*Time to flower*.—Plants flower continuously from late June to late September in an outdoor nursery in The Netherlands.

*Inflorescence longevity*.—Inflorescences maintain good substance for about three weeks on the plant; inflorescences persistent.

*Inflorescence buds*.—Height: About 3.2 cm. Diameter: About 4.4 cm. Shape: Broadly obovate with a flattened top. Color: Immature involucral bracts, close to 137A; immature ray florets, close to 154D with apices, close to 154B; immature receptacle spines, close to 146C with apices, close to 187A.

*Inflorescence size*.—Diameter: About 11.5 cm. Depth (height): About 3.7 cm. Disc diameter: About 4.5 cm.

*Receptacles*.—Height: About 1.1 cm. Diameter: About 1.4 cm. Shape: Broadly ovate. Color: Close to NN155A; towards the base, close to 145D.

*Ray florets*.—Quantity and arrangement: About 26 to 36 arranged in a single whorl at the base of the receptacle. Length: About 4.6 cm. Width: About 1.45 cm. Shape: Oblanceolate to narrowly oblong; slightly carinate. Apex: Emarginate to praemorse. Base: Cuneate. Margin: Entire. Texture and luster, upper surface: Smooth, glabrous; moderately velvety; matte. Texture and luster, lower surface: Smooth, glabrous; slightly glossy. Aspect: About −5° to 20° from horizontal. Color: When opening, upper surface: Close to 17B. When opening, lower surface: Close to 14D; towards the margins, close to 19B and margins at the base, close to N34C. Fully opened, upper surface: Close to 17C and towards the base, close to N34A; venation, similar to lamina colors; with subsequent development, color becoming closer to 13A and 14B and towards the base, closer to 47D. Fully opened, lower surface: Close to 18B; towards the margins, close to 16C and margins at the base, close to N34C; with subsequent development, color becoming closer to 11B and 11C and towards the base, flushed with close to N34C and basal margins, close to 59C.

*Disc florets*.—Quantity and arrangement: About 300 per inflorescence, arranged spirally at the center of the inflorescence. Length: About 1.1 cm. Diameter: About 2 mm. Shape: Tubular; distal 15% free, not fused. Apex: Acute. Base: Fused. Margin, free-part: Entire. Texture and luster, inner and outer surfaces: Smooth, glabrous; moderately glossy. Color, when opening, inner surface: Apex: Close to 143A and 143B; tips, close to 185A. Mid-section and base: Close to 145B with blotch, close to 185A. Color, when opening, outer surface: Apex: Close to 143B; tips, close to 185A. Mid-section and base: Close to 145B with blotch, close to 185B. Color, fully opened, inner surface: Apex: Close to 147B heavily flushed with close to 183A; tips, close to 183A. Mid-section and base: Close to N148B with blotch, close to 185A. Color, fully opened, outer surface: Apex: Close to 147B heavily flushed with close to 183A and 183B; tips, close to 183A and 183B. Mid-section and base: Close to N148B with blotch, close to 185A.

*Receptacle spines*.—Quantity: One per disc floret; about 300 per inflorescence. Length: About 1.3 cm. Diameter: About 1.5 mm. Shape: Acicular. Apex: Acute. Base: Attenuate. Texture and luster: Smooth, glabrous; glossy. Color: Apex: Close to N34A. Mid-section: Close to 143A. Base: Close to 145C.

*Involucral bracts*.—Quantity per inflorescence: About 90 arranged in about four whorls. Length: About 1.7 cm. Width: About 4 mm. Shape: Narrowly ovate; moderately to strongly reflexed. Apex: Acute. Base: Cuneate. Margin: Entire. Texture and luster, upper surface: Smooth, glabrous; margins, densely pubescent; slightly glossy. Texture and luster, lower surface: Sparsely to moderately pubescent; matte. Color, upper surface: Close to NN137A; centers, close to 138B. Color, lower surface: Close to NN137C; centers, close to 138B.

*Peduncles*.—Length: About 10.9 cm. Diameter: About 8 cm. Strength: Strong. Aspect: Mostly upright. Texture: Moderately to densely pubescent; strigose. Color: Close to 144A; moderately blotched, with blotches, close to 146A to 146B.

*Reproductive organs*.—Androecium (present on ray and disc florets): Quantity per floret: Five. Filament length: About 4 mm. Filament color: Close to 150D. Anther length: About 3.5 mm. Anther shape: Linear. Anther color: Close to 202A. Pollen amount: Moderate. Pollen color: Close to 17A. Gynoecium (present only on disc florets): Quantity per floret: One. Pistil length: About 7 mm. Stigma shape: Decurrent. Stigma color: Darker than N186C. Style length: About 6 mm. Style color: Close to 145D. Ovary color: Close to 157D. Seeds and fruits: To date, seed and fruit development have not been observed on plants of the new *Echinacea*.

Pathogen & pest resistance: To date, plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'IFECSSMS' as illustrated and described.

* * * * *